United States Patent [19]
Behar et al.

[11] Patent Number: 5,770,795
[45] Date of Patent: Jun. 23, 1998

[54] FLUID MIXTURE TESTING CELL SUITED FOR DETECTING PHASE CHANGES

[75] Inventors: Emmanuel Behar, Jouy Le Moutier; Gérard Moracchini, Andilly; José Sanchez, Viarmes, all of France

[73] Assignee: Institut Francais du Petrole, Rueil-Malmaison, France

[21] Appl. No.: 695,908

[22] Filed: Aug. 12, 1996

[30] Foreign Application Priority Data

Aug. 11, 1995 [FR] France .................................. 95 09814

[51] Int. Cl.$^6$ .................................................. G01N 11/10
[52] U.S. Cl. ...................... 73/54.23; 73/54.28; 73/54.35
[58] Field of Search .............................. 73/54.23, 54.02, 73/54.28, 54.31, 54.35

[56] References Cited

U.S. PATENT DOCUMENTS

| | | | |
|---|---|---|---|
| 5,303,578 | 4/1994 | Williams et al. | 73/54.23 X |
| 5,610,325 | 3/1997 | Rajagopal et al. | 73/54.35 X |

FOREIGN PATENT DOCUMENTS

| | | |
|---|---|---|
| 0544354 | 6/1993 | European Pat. Off. . |
| 1294950 | 4/1962 | France . |
| 2687223 | 8/1993 | France . |
| 754261 | 8/1980 | U.S.S.R. ............................... 73/54.35 |
| 1241102 | 6/1986 | U.S.S.R. ............................... 73/54.35 |

OTHER PUBLICATIONS

Research Disclosure No. 315 Jul. 1, 1990: ISSN 0374–4353 pp. 578, 1–578.2, "Phase Analysis Apparatus For Mixtures of Supercritical Fluids and Polymer Solutions" & WPI Database, Section CH, Week 9032.
Patent Abstracts of Japan, vol. 010, No. 072, (P–438), Arch 22, 1986 & JP-A-60 210751.
Ias '93, Proceedings of IEEE Industry Application Society 28th Annual Meeting (IEEE Cat. No. 93CH3366–2), vol. 3, ISBN 0–7803–1462–X, 1993, IEEE, New York, NY USA, pp. 1779–1784, Yatsuzuka K. et al.

*Primary Examiner*—Hezron E. Williams
*Assistant Examiner*—Daniel S. Larkin
*Attorney, Agent, or Firm*—Antonelli, Terry, Stout & Kraus, LLP

[57] ABSTRACT

A mixture containing substances likely to settle or to flocculate is fed into a chamber (1a) of a body (1) delimited by a mobile piston (18) and a closed-circuit circulation of the mixture is established by means of a homogenization turbine (8) driven by a motor (28) associated with magnetic driving means (9, 26). According to the pressure and to the temperature, variations in the conductance of the mixture flowing between two electrodes (1, 16) connected to a measuring device (17) are measured on the one hand and variations in the driving torque applied to turbine (8) under the effect of the concomitant variations in the apparent viscosity of the mixture are measured on the other hand. The cell can be used to study of the conditions of formation of asphaltene deposits or flocculations in petroleum crudes for example.

17 Claims, 1 Drawing Sheet

FLUID MIXTURE TESTING CELL SUITED FOR DETECTING PHASE CHANGES

FIELD OF THE INVENTION

The present invention relates to a cell suited for detecting phase discontinuities occurring in mixtures.

The flocculometer according to the invention can notably be used to detect the appearance and the extent of asphaltene deposits or flocculations in asphaltene-rich petroleum crudes.

It is important for oil producers who have to convey fluids from production fields by means of production wells and pipeline networks to know the temperature and pressure thresholds below which asphaltenes settle, so as to optimize production and transfer conditions.

BACKGROUND OF THE INVENTION

Prior art examples in the field of cells for monitoring mixture consistency are described for example in patents EP-A-544,354 and 551,145.

Among the well-known processes allowing to monitor changes of state of a mixture, and notably to detect the formation of flocculations, optical processes may for example be cited. The variation in the absorption coefficient or absorbance of light rays in the visible frequency domain or in the infrared, which occurs during such consistency changes, is detected. In case of particularly opaque mixtures, such as asphaltene-rich petroleum crudes, they must necessarily be previously diluted. Besides, the process is not very selective since it does not allow the variation in the optical transmittance of the mixture to be related to a precise absorbent substance. The variation in the optical transmissivity of petroleum crudes in particular can be affected by other substances than asphaltenes.

It is also well-known to monitor variations in the compositions of mixtures by means of an electric type method which takes advantage of the variation in the electrical conductivity of the mixtures as a function of the composition thereof. This method is notably applied to petroleum crudes in order to detect the formation of asphaltenes. The mixture to be analyzed is pumped through pipes up to a measuring cell. It circulates between two concentric plates or cylinders that lie at a short distance from one another and form two electrodes connected to a conductivity measuring instrument.

In case of laboratory measurements, the vessel containing the mixture to be analyzed, the circulation pump and the measuring cell can be installed for example inside a thermostat-controlled enclosure. Within the scope of in-situ measurements conducted on lines such as pipelines, the mixture to be analyzed is diverted by means of a circuit provided with valves and a pump to a conductance or capacitance variation measuring cell prior to being optionally reinjected.

In existing electric conductance measuring installations, the pump is generally separate from the measuring cell and connected thereto by pipes, and the conductance measurements are performed on the fluid following a continuous circulation through the cell. The length of the circuit between the elements and possible level differences between them favour the formation of deposits, all the more so as the mixture contains solid or pasty substances. The fluid flowing through the cell often lacks homogeneity, which affects the measurement quality. Electric conductance measurements are sometimes completed by viscosity measurements in a viscometer separate from the cell.

SUMMARY OF THE INVENTION

The cell according to the invention allows to test the consistency of a mixture consisting for example of an asphaltene-rich petroleum crude while avoiding the drawbacks of previous cells. It comprises a body provided with a cylindrical inner cavity, means for feeding the mixture into the inner cavity, and two coaxial electrodes placed inside one another, between which the mixture flows, these electrodes being connected to a device for measuring the electric conductivity.

The cell is characterized in that the inner electrode is tubular and contains a homogenization means or turbine suited for establishing a closed circulation of the mixture between the two electrodes, means for driving the turbine and means for measuring the apparent viscosity of the circulating mixture.

The turbine comprises for example a tubular element internally provided with a helix (a helical element added in a tube for example or a tube internally provided with a helical groove). The means for measuring the apparent viscosity can comprise, for example, an element for measuring the driving torque applied to the turbine.

The cell preferably comprises means for applying a determined pressure to the mixture, comprising for example a piston sliding tightly in the body, the volume of the body above the piston being intermittently connected to an element delivering a hydraulic fluid under pressure 33, such as a hydraulic pump P and a device measuring the displacement of the piston.

According to an embodiment, the means for driving the turbine comprise a motor exterior to the body of the cell, associated with contactless coupling means co-operating with the turbine and the motor.

According to an embodiment, the body of the cell is made of a conducting material and forms one of the electrodes, the other electrode being supported by an insulating ring fastened to the body of the cell.

The conductance and viscosity measurements obtained by means of the cell are particularly precise and stable since they are conducted on a well homogeneous mass brought into convection in a closed chamber of relatively small volume, which can be easily maintained at a constant temperature and pressure. More precise analysis of the deposition and flocculation phenomena allows their appearance to be more readily prevented in hydrocarbon transportation networks.

BRIEF DESCRIPTION OF THE DRAWINGS

Other features and advantages of the cell according to the invention will be clear from reading the description hereafter of an embodiment given by way of non limitative example, with reference to the accompanying drawings in which.

DESCRIPTION OF THE INVENTION

Figures 1, 2:
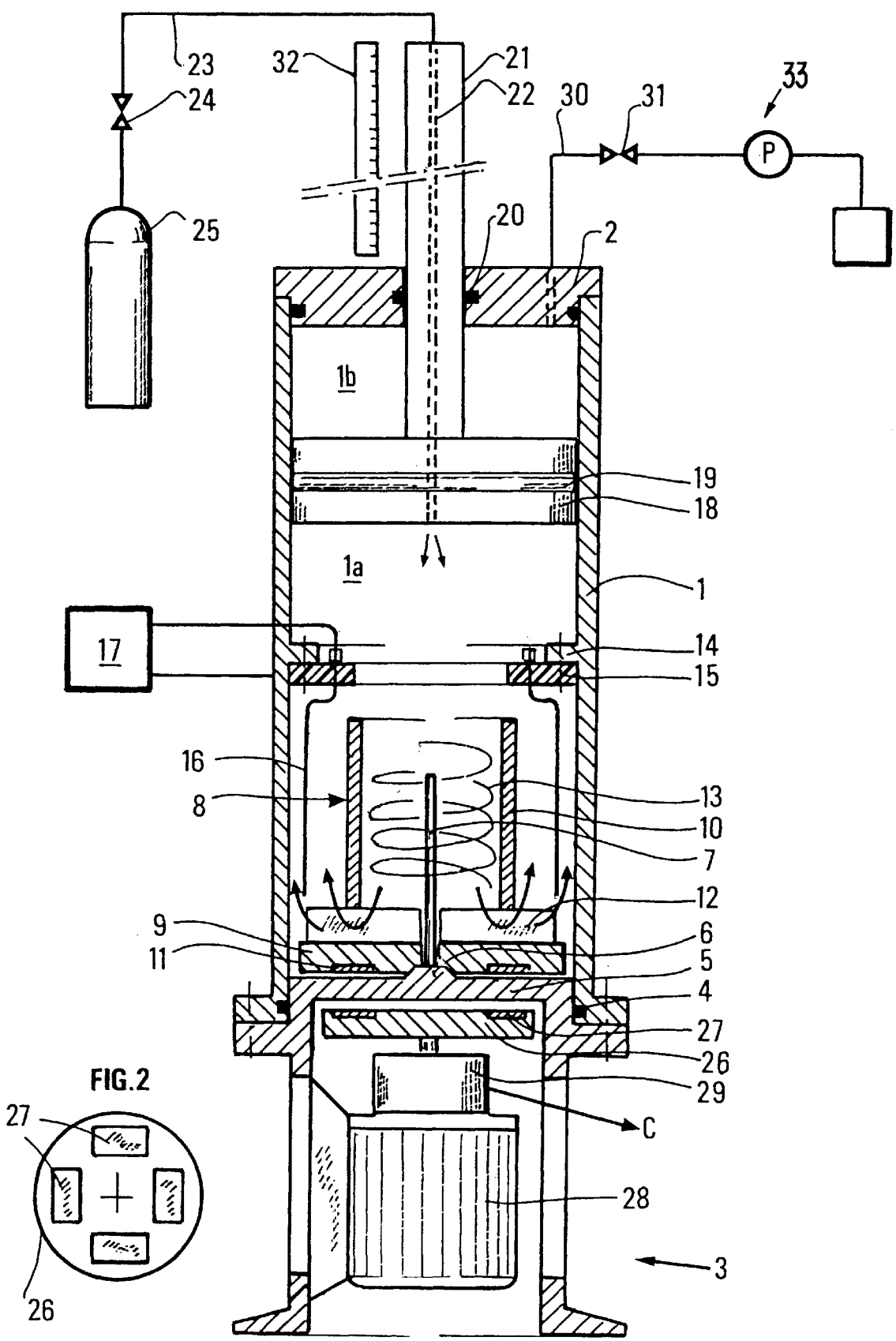
FIG. 1 shows a cross section of the test cell.
FIG. 2 shows the layout of the magnets on the magnetic driving plates.

The cell comprises (FIG. 1) a rigid tubular body arranged vertically, that is closed at a first end by a wall 2. It is made of an electricity conducting material. The opposite end thereof is open and provided with means for fastening it to a baseplate 3 made of a non-magnetic material, by means of seals 4. The upper wall 5 of baseplate 3 is provided with a centering bulb 6 extended by a thin rod 7. A rotating assembly 8 comprising a bedplate 9 surmounted by a tubular part 10 rests on centering bulb 6. Magnets 11 are fastened to the lower wall thereof (FIG. 1). The upper wall thereof is provided with fins 12. A helix 13 is fastened to the inner wall of tubular part 10.

The inner wall of body 1 comprises a shoulder 14 to which a ring 15 made of an insulating material is fastened. A tubular electrode 16 is fastened to this ring 15 and it is electrically linked to a first terminal of an electrical impedance measuring instrument 17. The other terminal thereof is linked to the conducting body 1.

A piston 18 provided with a seal 19 slides in the upper part of body 1. It forms the upper limit of a variable-volume chamber 1'*a*. The upper wall 2 of the body is provided with an opening fitted with seals 20 through which a rod 21 integral with piston 18 can slide. Rod 21 is provided with an axial channel 22 to which is connected a flexible tube 23 connected, by means of a valve 24, to a vessel 25 containing a mixture to be analyzed.

A disk plate 26 provided with magnets 27 (FIG. 2), that is brought into rotation by an electric motor 28, lies below the upper wall 5 of baseplate 3. An element 29 is placed on the motor shaft in order to measure the driving torque applied to disk 26. By magnetic action through the wall 5 of baseplate 3, the rotating motion of disk 26 (see "c" in FIG. 1) is transmitted to the bedplate 9 of turbine 8.

The volume 1*b* of the body above piston 18 communicates, by means of a line 30 controlled by a valve 31, with a pump P delivering a hydraulic fluid under pressure. Mobile piston 18 is moved by controlled injection of this fluid.

A displacement measuring means 32, of optical type for example, is placed in the neighbourhood of rod 21 in order to measure the displacement thereof and to deduce therefrom the concomitant volume variation of the chamber 1*a* of the body.

The previous assembly is preferably placed in an isothermal enclosure that is not shown.

Operation:

1) The mixture to be analyzed, maintained under pressure in vessel 25, is injected into the chamber 1*a* of the body through the axial channel 22 of the rod and piston 18.

2) The motive means (P) are then actuated in order to lower the piston and to restore, in chamber 1*a*, a pressure above the bubble-point pressure.

3) The electric motor 28 is then actuated, so as to run turbine 8 by magnetic transmission at constant speed. The mixture is stirred in closed circuit between the inside and the outside of turbine 8. It thus circulates permanently between the outer electrode consisting of body 1 and the coaxial inner electrode 16, and impedance meter 17 measures the variations in the conductance thereof in time. The variations with time in the apparent viscosity of the mixture maintained homogeneous by the stirring, that varies like the driving torque applied, are also measured.

In cases where the mixture consists of asphaltene-rich petroleum crudes, the flocculations occurring therein as a function of the pressure and of the temperature imposed can be precisely detected.

Without departing from the scope of the invention, body 1 can be made of a non-conducting material, the outer electrode consisting of a tube made of a conducting material lining the inner wall of chamber 1*a*, or direct mechanical connections can be used to drive the turbine, or a tube 10 provided with a helical groove on the inner wall thereof can be used to form the stirring helix 13.

What is claimed is:

1. A test cell for testing a fluid mixture suited for detecting phase discontinuities occurring in said mixture, comprising a body provided with a cylindrical inner cavity, means for feeding the mixture into the inner cavity, two coaxial electrodes including a tubular inner electrode and an outer electrode, said inner and outer electrodes being electrically insulated and connected to an electrical conductivity measuring device, a mixing means including a tubular element internally provided with a helix, placed inside the tubular inner electrode and suitable for establishing a closed circulation of the mixture between the inner and outer electrodes, to provide a circulating mixture, means for driving the mixing means in rotation and means for measuring an apparent viscosity of the circulating mixture.

2. A test cell as claimed in claim 1, wherein said mixing means includes a tube and a helical element added inside said tube.

3. A test cell as claimed in claim 1, wherein said mixing means includes a tube and said helix is a helical groove provided in the inner wall of said tube.

4. A test cell as claimed in claim 3, wherein said mixing means includes a rotating plate provided with fins.

5. A test cell as claimed in claim 3, wherein said means for measuring an apparent viscosity comprises a means for measuring driving torque applied to the mixing means.

6. A test cell as claimed in claim 3, including means for applying a determined pressure to the mixture in said inner cavity.

7. A test cell as claimed in claim 3, including a piston sliding tightly in said inner cavity and pressure means for driving the piston, resulting in a determined pressure being applied to the mixture in said inner cavity.

8. A test cell as claimed in claim 3, including means for driving the mixing means including a motor outside said body, and a contactless coupling means for coupling said motor and said mixing means.

9. A test cell as claimed in claim 3, including an insulating ring fastened to the body, said body being made of a conducting material and forms said outer electrode, the inner electrode being supported by said insulating ring.

10. A test cell as claimed in claim 1, wherein said mixing means includes a rotating plate provided with fins.

11. A test cell as claimed in claim 1, wherein said means for measuring an apparent viscosity comprises a means for measuring driving torque applied to the mixing means.

12. A test cell as claimed in claim 1, including means for applying a determined pressure to the mixture in said inner cavity.

13. A test cell as claimed in claim 1, including a piston sliding tightly in said inner cavity and pressure means for driving the piston, resulting in a determined pressure being applied to the mixture in said inner cavity.

14. A test cell as claimed in claim 1, including means for driving the mixing means including a motor outside said body, and a contactless coupling means for coupling said motor and said mixing means.

15. A test cell as claimed in claim 1, including an insulating ring fastened to the body, said body being made of a conducting material and forms said outer electrode, the inner electrode being supported by said insulating ring.

16. A test cell for testing a fluid mixture suited for detecting phase discontinuities occurring in said mixture, comprising a body provided with a cylindrical inner cavity, means for feeding the mixture into the inner cavity, two coaxial electrodes including a tubular inner electrode and an outer electrode in the inner cavity, said inner and outer electrodes being electrically insulated and connected to an electrical conductivity measuring device, a mixing means including a tubular element internally provided with a helix, placed inside the tubular inner electrode in the inner cavity and suitable for establishing a closed circulation of the mixture between the inner and outer electrodes, to provide a circulating mixture, means for driving the mixing means in rotation and means for measuring an apparent viscosity of the circulating mixture.

17. The test cell as claimed in claim 16, wherein said means for feeding is a means for feeding an asphaltene petroleum crude.

* * * * *